United States Patent
Oishi et al.

(10) Patent No.: US 9,737,494 B2
(45) Date of Patent: Aug. 22, 2017

(54) METHOD OF REGULATING CIRCADIAN RHYTHM, AND METHOD OF PREPARING CIRCADIAN RHYTHM REGULATORY AGENT

(71) Applicants: National Institute of Advanced Industrial Science & Technology, Tokyo (JP); Nisshin Seifun Group Inc., Tokyo (JP); Oriental Yeast Co., Ltd, Tokyo (JP)

(72) Inventors: Katsutaka Oishi, Ibaraki (JP); Koyomi Miyazaki, Ibaraki (JP); Yoshiaki Onishi, Ibaraki (JP); Tatsunosuke Tomita, Ibaraki (JP); Nanako Itoh, Ibaraki (JP); Shinichi Fukudome, Fujimino (JP); Keiko Tanaka, Fujimino (JP); Yosuke Kikuchi, Fujimino (JP); Kenji Kasuya, Tokyo (JP)

(73) Assignees: NAT'L INSTITUTE OF ADVANCED INDUSTRIAL SCIENCE & TECHNOLOGY, Tokyo (JP); NISSHIN SEIFUN GROUP INC., Tokyo (JP); ORIENTAL YEAST CO., LTD., Tokyo (JP)

( * ) Notice: Subject to any disclaimer, the term of this patent is extended or adjusted under 35 U.S.C. 154(b) by 54 days.

(21) Appl. No.: 14/676,265

(22) Filed: Apr. 1, 2015

(65) Prior Publication Data
US 2015/0306045 A1 Oct. 29, 2015

Related U.S. Application Data

(62) Division of application No. 13/889,656, filed on May 8, 2013, now abandoned.

(30) Foreign Application Priority Data

May 15, 2012 (JP) .................................. 2012-111161
Nov. 1, 2012 (JP) .................................. 2012-241533

(51) Int. Cl.
| | | |
|---|---|---|
| C07C 39/08 | (2006.01) | |
| A61K 31/05 | (2006.01) | |
| A61K 36/185 | (2006.01) | |

(52) U.S. Cl.
CPC ............ *A61K 31/05* (2013.01); *A61K 36/185* (2013.01); *C07C 39/08* (2013.01); *A61K 2236/33* (2013.01)

(58) Field of Classification Search
None
See application file for complete search history.

(56) References Cited

U.S. PATENT DOCUMENTS

| | | |
|---|---|---|
| 6,582,594 B1 | 6/2003 | Collins et al. |
| 2003/0150805 A1 | 8/2003 | Collins et al. |
| 2006/0073187 A1 | 4/2006 | Akimoto et al. |

FOREIGN PATENT DOCUMENTS

| | | |
|---|---|---|
| JP | 2001-302505 | 10/2001 |
| JP | 2002-500088 | 1/2002 |
| JP | 2009-084192 | 4/2009 |

OTHER PUBLICATIONS

Umegaki et al., "Ginkgo Biloba Extract Attenuates the Development of Hypertension in Deoxycorticosterone Acetate-Salt Hypertensive Rats," Clinical and Experimental Pharmacology and Physiology (2000) 27, 277-282.*

Zarnowska et al., "Alkylresorcinols in Fruit Pulp and Leaves of *Ginkgo biloba* L.," Z Naturforsch C, 55 (11-12), 881-885, Nov.-Dec. 2000.*

Zheng et al., "FOXO and insulin signaling regulate sensitivity of the circadian clock to oxidative stress," PNAS, Oct. 2, 2007, vol. 104, No. 40, pp. 15899-15904.

Arkadiusz Kozubek et al., Resorcinolic Lipids, the Natural Non-isoprenoid Phenolic Amphiphiles and Their Biological Activity, Chemical Reviews, vol. 99, No. 1, pp. 1-25, Jan. 1999.

Alastair B. Ross et al., Dietary Alkylresorcinols: Absorption, Bioactivities, and Possible Use as Biomarkers of Whole-grain Wheat- and Rye-rich Foods, Lead Review Article, vol. 62, No. 3, pp. 81-95, Mar. 2004.

(Continued)

*Primary Examiner* — Paul A Zucker
*Assistant Examiner* — Mark Luderer
(74) *Attorney, Agent, or Firm* — Young & Thompson

(57) ABSTRACT

Disclosed are a method of preparation and method of application of a circadian rhythm regulatory agent having as an active ingredient an alkylresorcinol represented by general formula (I) below and a circadian rhythm regulatory agent containing as an active ingredient an alkylresorcinol-containing extract from a cereal or a nut containing an alkylresorcinol of the following general formula (I). In the following general formula (I), $R_1$ is a saturated or unsaturated alkyl group; and $R_2$ is hydrogen or methyl. In general formula (I), $R_1$ is preferably at the para-position with respect to $R_2$, and $R_1$ is preferably a saturated or unsaturated alkyl group having 15 to 27 carbon atoms.
[Chem. 1]

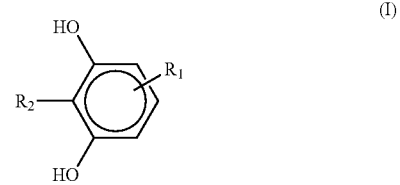

2 Claims, 3 Drawing Sheets

(56) References Cited

OTHER PUBLICATIONS

Francisco, "Application of supercritical carbon dioxide for the extraction of alkylresorcinois from rye bran", J. of Supercritical Fluids 35 (2005) 220-226.
Ross et al., "Alkylresorcinols in Cereals and Cereal Products." J. Agric. Food chem., 51, 4111-4118, 2003.
Kozubek et al. "Resorcinolic Lipids, the Natural Non-isoprenoid Phenolic Amphiphiles and Their Biological Activity," Chemical Reviews, 99 (1), 1-26, 1999.

* cited by examiner

METHOD OF REGULATING CIRCADIAN RHYTHM, AND METHOD OF PREPARING CIRCADIAN RHYTHM REGULATORY AGENT

TECHNICAL FIELD

This invention relates to a circadian rhythm regulatory agent for regulating biological circadian rhythm. The circadian rhythm regulatory agent of the invention contains an alkylresorcinol(s) as an active ingredient.

BACKGROUND

There are known many diseases caused by circadian rhythm disorders. Various types of circadian rhythm regulatory agents have been proposed to alleviate these diseases.

For example, a circadian rhythm regulatory agent containing an endocrine hormone, such as melatonin, is known. However, treatment with endocrine hormones has a safety problem on account of the risk of side effects so that a material with high safety has been sought for.

Sleep disorders which are now a social issue include circadian rhythm sleep disorders. To basically remedy circadian rhythm sleep disorders, a material that regulates the diurnal cycle has been demanded.

There are reports on circadian rhythm regulatory agents of food origin. For example, patent literature 1 below discloses a composition containing as an active ingredient cryptoxanthin extracted from satsuma orange (*Citrus unshiu*) and/or an ester thereof and having a circadian clock normalizing effect. Patent literature 2 below discloses a circadian rhythm normalizing composition having arachidonic acid-containing fat and oil as an active ingredient.

Synthetic alkylresorcinols and derivatives thereof and alkylresorcinol-containing extracts from the hull of cereal grains, such as wheat and rye, or the shell of nuts, such as cashew nuts, are reported to have anti-obesity effect, antioxidant effect, anti-immune effect, and the like. However, it is unknown that alkylresorcinols exhibit circadian rhythm regulatory effects.

Alkylresorcinols are reported to be present in a wide range of plants as resorcinol-lipids that are natural, non-isoterpenoid phenolic, amphiphilic compounds (see non-patent literature 1 below). The non-patent literature 1 reports that the plants as a source of resorcinol lipids include those belonging to the families Anacardiaceae, Ginkgoaceae, Proteaceae, Myrsinaceae, Primulaceae, Myristicaceae, Iridaceae, Araceae, Artemisia of Compositae, Fabaceae, and Poaceae. With respect to the toxicity of alkylresorcinols, non-patent literature 2 below reports that no apparent toxicity is observed in oral administration to rats of 5 g/kg-b.w. of 4-alkylresorcinol having a saturated C15 alkyl group of cashew nut shell origin.

CITATION LIST

Patent Literature

Patent literature 1: JP 2009-084192A
Patent literature 2: US 2006073187A1

Non-Patent Literature

Non-patent literature 1: Arkadiusz Kozubek et. al., Chemical Reviews, vol. 99, No. 1, pp. 1-25 (1999)

Non-patent literature 2: Alastair B. Ross, et al., Nutrition Review, vol. 62, No. 3, pp. 81-95(2004)

SUMMARY OF INVENTION

Technical Problem

The invention relates to a circadian rhythm regulatory agent of food origin that is safe and secure even when taken for a long period of time.

Solution to Problem

As a result of extensive investigations, the present inventors have found that an alkylresorcinol or a cereal extract containing alkylresorcinols is influential on expression of circadian clock gene and circadian activity rhythm.

Based on the above finding, the invention provides a circadian rhythm regulatory agent containing alkylresorcinols represented by general formula (I) shown below as an active ingredient. The invention also provides a circadian rhythm regulatory agent containing, as an active ingredient, an alkylresorcinol-containing extract obtained from a cereal or a nut containing alkylresorcinols represented by general formula (I).

[Chem. 1]

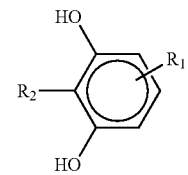

(I)

wherein $R_1$ represents a saturated or unsaturated alkyl group; and $R_2$ represents a hydrogen atom or a methyl group.

Advantageous Effects of Invention

The circadian rhythm regulatory agent of the invention is effective in regulating circadian rhythm disorder to normalize biological diurnal rhythm. The alkylresorcinol or alkylresorcinol-containing extract as an active ingredient has high safety with no side effects so that the agent of the invention has the advantage of involving no problem in use.

The circadian rhythm regulatory agent of the invention is effective in treating a circadian rhythm sleep disorder.

DESCRIPTION OF EMBODIMENTS

Figure 1:
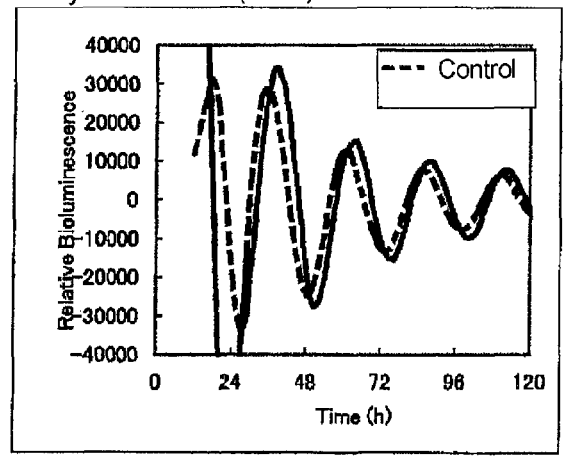
FIG. 1 is a graph showing the influence of the circadian rhythm regulatory agent of Example 1 (synthetic alkylresorcinol) on expression of circadian clock genes.

The circadian rhythm regulatory agent of the invention contains alkylresorcinols represented by general formula (I) as an active ingredient. The alkylresorcinols are effective in regulating circadian rhythm disorders to normalize biological diurnal rhythm. That is, the alkylresorcinols have a circadian rhythm regulatory effect.

In general formula (I), while the saturated or unsaturated alkyl group as represented by $R_1$ is not limited by the number of carbon atoms, the number of carbon atoms of $R_1$ is preferably 15 to 27, more preferably 15 to 25.

Representative examples of the C15-27 saturated alkyl groups include straight-chain alkyl groups, such as n-pentadecyl, n-heptadecyl, n-nonadecyl, n-heneicosyl, n-tricosyl, n-pentacosyl, and n-heptacosyl. Branched or cyclic alkyl groups are also useful. Preferred of them are C15-25 saturated alkyl groups, with C15-25 straight-chain saturated alkyl groups being more preferred.

The C15-27 unsaturated alkyl groups include those corresponding to the above recited C15-27 saturated alkyl groups. The number and position of the unsaturated bonds in the unsaturated alkyl group are not particularly limited.

In general formula (I), $R_2$ is preferably a hydrogen atom. $R_1$ is preferably at the para-position to $R_2$.

Specific examples of the alkylresorcinol represented by general formula (I) that can be used as an active ingredient of the circadian rhythm regulatory agent of the invention are listed below:
1,3-Dihydroxy-5-n-pentadecylbenzene (C15:0)
1,3-Dihydroxy-5-n-heptadecylbenzene (C17:0)
1,3-Dihydroxy-5-n-nonadecylbenzene (C19:0)
1,3-Dihydroxy-5-n-heneicosylbenzene (C21:0)
1,3-Dihydroxy-5-n-trico sylbenzene (C23:0)
1,3-Dihydroxy-5-n-pentaco sylbenzene (C25:0)
1,3-Dihydroxy-5-n-heptaco sylbenzene (C27:0)

Particularly preferred of the alkylresorcinols of general formula (I) are those in which $R_1$ is a C15-25 saturated alkyl group, and $R_2$ is hydrogen atom. Especially preferred are 1,3-dihydroxy-5-n-pentadecylbenzene (C15:0), 1,3-dihydroxy-5-n-heptadecylbenzene (C17:0), 1,3-dihydroxy-5-n-nonadecylbenzene (C19:0), 1,3-dihydroxy-5-n-heneicosylbenzene (C21:0), 1,3-dihydroxy-5-n-tricosylbenzene (C23:0), and 1,3-dihydroxy-5-n-pentacosylbenzene (C25:0).

The alkylresorcinol of general formula (I) can be synthesized in a usual manner or may be a commercially available product. An extract prepared from a plant in a usual manner is also useful. Plants containing alkylresorcinols include those of the families Anacardiaceae, Ginkgoaceae, Proteaceae, Myrsinaceae, Primulaceae, Myristicaceae, Iridaceae, and Araceae, the genus Artemisia of the family Compositae, and the families Fabaceae and Poaceae. Inter alia, plants of the family Poaceae have been under researches with respect to alkylresorcinols as an edible effective component and are therefore suitable as a source of the active ingredient for use as a circadian rhythm regulatory agent of the invention. Of the plants of the family Poaceae particularly preferred as a source are wheat and rye because of their high contents of the alkylresorcinols of general formula (I) ranging from about 0.015% of 0.3% by mass based on the whole grain weight.

Nuts, such as cashew nuts, are also suitable as alkylresorcinols source, the active ingredient of the circadian rhythm regulatory agent of the invention.

In using an alkylresorcinol-containing extract prepared from cereals or nuts as an active ingredient, an alcoholic extract is preferred.

The manner for extracting with an alcohol is not particularly limited, including, for example, a method in which the gramineous plant seeds are immersed, stirred, or refluxed in an alcohol or a supercritical fluid extraction method.

Examples of alcohols used for extraction include those that are liquid at room temperature, such as lower alcohols, e.g., methanol, ethanol, n-propanol, isopropyl alcohol, and n-butanol, and polyhydric alcohols, e.g., 1,3-butlene glycol, propylene glycol, and glycerol. Ethanol is preferred in terms of convenience of use and environmental friendliness. The alcohols include those containing an aqueous component, namely, aqueous alcohols. The alcohol content of the aqueous alcohols is usually 70 vol % or more, preferably 80 vol % or more, more preferably 90 vol % or more. The extraction may be carried out in the usual manner.

The circadian rhythm regulatory agent of the invention contains the alkylresorcinols of general formula (I) as an active ingredient and, optionally, other pharmaceutically acceptable ingredients including carriers, excipients, stabilizers, and other additives and ingredients. The circadian rhythm regulatory agent of the invention may be formulated into preparations in a usual manner. Specifically, it can be formulated into dosage forms including oral dosage forms, such as tablets, powders, granules, and capsules, and parenteral dosage forms, such as injectable solutions that are prepared by dissolving the alkylresorcinol of general formula (I) in sterilized distilled water or sterilized physiological saline together with a solubilizing agent and sealing the solution in an ampule. As other ingredients, substances having other medicinal effects, various vitamins, crude drugs, and minerals may be added appropriately in amounts that do not impair the circadian rhythm regulating effects of the invention.

The content of the active ingredient in the circadian rhythm regulatory agent of the invention is not particularly limited and may be selected as appropriate to the dosage form, the symptoms, age, and sex of a subject to be given the agent, and other factors. In administering the agent to a human, a recommended dosage of the active ingredient of the circadian rhythm regulatory agent of the invention is usually 0.01 to 10 g per day for an adult.

EXAMPLES

The invention will now be illustrated in greater detail with reference to Examples and Test Examples, but it should be understood that the invention is not limited thereto.

Example 1

Synthetic 1,3-Dihydhroxy-5-n-pentadecylbenzene (C15:0) manufactured by Researchem and purchased from Namiki Shoji Co., Ltd. was used as a circadian rhythm regulatory agent.

Example 2

An alkylresorcinol-containing ethanolic bran extract was prepared from bran according to the following extraction method. The extract was used as a circadian rhythm regulatory agent. The alkylresorcinols contained in the extract were found to be composed mainly of 1,3-dihydroxy-5-n-pentadecylbenzene (C15:0), 1,3-dihydroxy-5-n-heptadecylbenzene (C17:0), 1,3-dihydroxy-5-n-nonadecylbenzene (C19:0), 1,3-dihydroxy-5-n-heneico sylbenzene (C21:0), 1,3-dihydroxy-5-n-tricosylbenzene (C23:0), and 1,3-dihydroxy-5-n-pentaco sylbenzene (C25:0).

Extraction Method:

To the bran was added five times by mass the amount of ethanol, and the mixture was shaken at 150 rpm for 2 hours at room temperature to extract. The mixture was centrifuged at 3500 rpm for 15 minutes at room temperature, and the supernatant was dried in a centrifugal concentrator. The resulting concentrate was weighed and dissolved in ethanol in a concentration of 420 mg/ml to provide an alkylresorcinol-containing ethanolic bran extract.

Example 3

An alkylresorcinol-containing ethanolic rye extract was prepared in the same manner as in Example 2, except for replacing the bran with rye and dissolving the concentrate in ethanol in a concentration of 110 mg/ml. The extract was used as a circadian rhythm regulatory agent. The alkylresorcinols contained in the extract were composed mainly of 1,3-dihydroxy-5-n-pentadecylbenzene (C15:0), 1,3-dihydroxy-5-n-heptadecylbenzene (C17:0), 1,3-dihydroxy-5-n-nonadecylbenzene (C19:0), 1,3-dihydroxy-5-n-heneico sylbenzene (C21:0), 1,3-dihydroxy-5-n-trico s ylbenzene (C23:0), and 1,3-dihydroxy-5-n-pentacosylbenzene (C25:0).

Example 4

An alkylresorcinol-containing ethanolic bran extract was prepared from a wheat bran according to the following extraction method. The extract was used as a circadian rhythm regulatory agent. The alkylresorcinols contained in the extract were composed mainly of 1,3-dihydroxy-5-n-pentadecylbenzene (C15:0), 1,3-dihydroxy-5-n-heptadecylbenzene (C17:0), 1,3-dihydroxy-5-n-nonadecylbenzene (C19:0), 1,3-dihydroxy-5-n-heneico sylbenzene (C21:0), 1,3-dihydroxy-5-n-tricosylbenzene (C23:0), and 1,3-dihydroxy-5-n-pentaco sylbenzene (C25:0).

Extraction Method:

To the bran was added five times by mass the amount of ethanol and stirred at 600 rpm for 16 hours at room temperature to extract. The mixture was filtered to remove unnecessary matter to give an ethanolic extract. Ethanol was removed by evaporation to give a solvent extract.

The resulting ethanolic bran extract was purified by medium-pressure chromatography under the conditions below. Peak components appearing during the period of 31 to 36 minutes from the start of elution were collected, and the solvent was removed by evaporation to give an alkylresorcinol-containing ethanolic bran extract.

Conditions of medium-pressure chromatography:

Column: silica gel (Inject Column 3 L+Hi-Flash Column 5 L; pore size: 60 Å; particle size: 40 nm; available from Yamazen Corp.)

Mobile phase: hexane/ethyl acetate=90/10 (by volume) for 9 minutes; 80/20 for 15 minutes; and 60/40 for 16 minutes Detection wavelength: 254 nm

Test Example 1

The circadian rhythm regulatory agents of Examples 1 to 3 (i.e., 1,3-dihydroxy-5-n-pentadecylbenzene, alkylresorcinol-containing ethanolic bran extract, and alkylresorcinol-containing ethanolic rye extract) were evaluated for the influence on expression of circadian clock gene in accordance with the following test method. The results obtained are shown in FIGS. 1 to 3, respectively.

As is apparent from FIG. 1, addition of 1,3-dihydroxy-5-n-pentadecylbenzene delays the circadian rhythm phase of Bmall expression and shortens the cycle by 0.5 hours.

Figure 2:
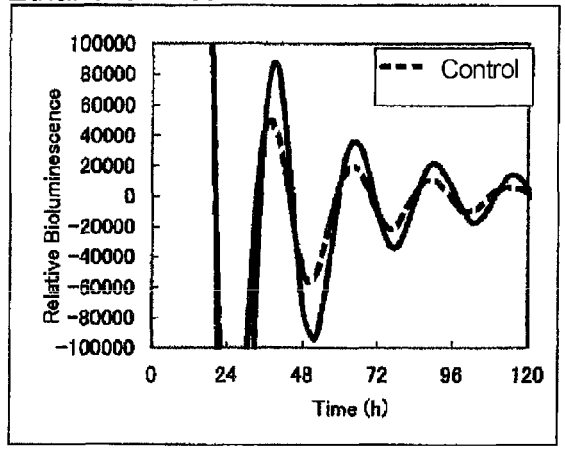
FIG. 2 is a graph showing the influence of the circadian rhythm regulatory agent of Example 2 (alkylresorcinol-containing ethanolic extract of a wheat bran prepared by extracting the bran with ethanol) on expression of circadian clock gene.
Figure 3:
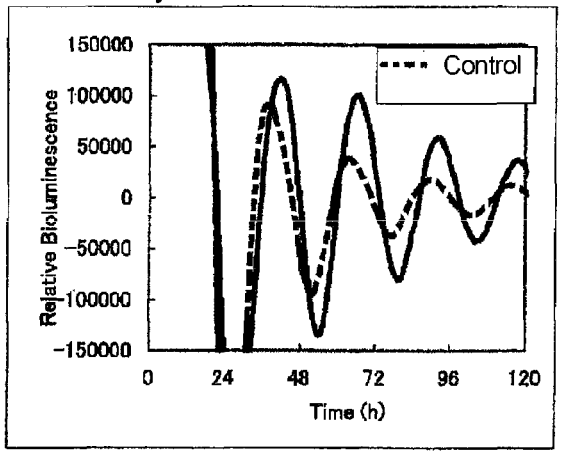
FIG. 3 is a graph showing the influence of the circadian rhythm regulatory agent of Example 3 (alkylresorcinol-containing ethanolic extract of rye prepared by extracting rye with ethanol) on expression of circadian clock gene.

As is apparent from FIG. 2, addition of the alkylresorcinol-containing ethanolic bran extract increases the amplitude of the circadian rhythm of Bmall expression. As is apparent from FIG. 3, addition of the alkylresorcinol-containing ethanolic rye extract delays the phase of the circadian rhythm of Bmall expression and increases the amplitude of the rhythm.

Test Method:

To prepare a recombination vector, the promoter regions of a clock gene Bmall (−97 to +27 regions including the RORE sequence and the transcription initiation site) were inserted into a luciferase luminescence vector containing a PEST sequence serving as a signal for rapid degradation of expressed proteins (pGL3-dLuc, from Promega). About $5 \times 10^5$ cells of mouse fibroblast cell line NIH3T3 were inoculated into a 35 mm diameter culture dish. After culturing for 24 hour, the recombination vector was transfected into the cells.

Screening of candidate substances was performed using the culture cells. After 24 hours from the transfection, the cells were cultured under stimulation in a medium containing 100 nM dexamethasone for 2 hours so as to synchronize the rhythmic phase of each cell. Then, a test substance was added to a medium containing a luciferin, (a luminescence substrate of the NIH3T3 cell line), and chemiluminescence by the reporter genes was measured in real-time while continuing the cell culture. The test substances were 1,3-dihydroxy-5-n-pentadecylbenzene, the alkylresorcinol-containing ethanolic bran extract, and the alkylresorcinol-containing ethanolic rye extract. The 1,3-dihydroxy-5-n-pentadecylbenzene was dissolved in ethanol in a concentration of 25 mM, and the solution was added to the medium in a concentration of 12.5 μM. Each of the alkylresorcinol-containing ethanolic bran extract and the alkylresorcinol-containing ethanolic rye extract was dissolved in ethanol in a concentration of 420 mg/ml and 110 mg/ml, respectively, and the solution was added to the medium in a concentration of 1.68 mg/ml and 0.33 mg/ml, respectively. As a control, ethanol, which is the solvent of the test substance, was added at the same timing, and the changes in amount of luminescence were compared. Luminescence was measured for one minute at 10 minute interval using AB-2550 Kronos Dia from ATTO Corp.

Test Example 2

Figure 4:
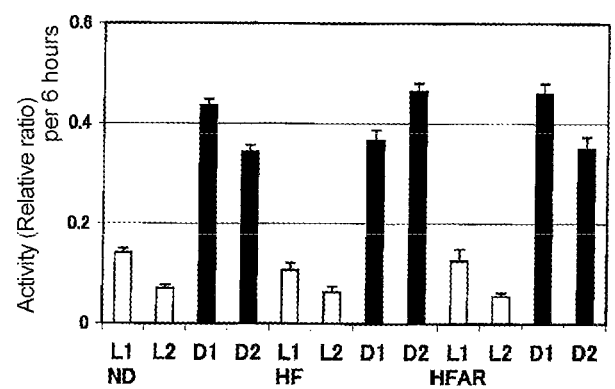
FIG. 4 is a graph showing the influence of the alkylresorcinol-containing ethanolic extract of the on drinking behavior rhythm in mice fed a high-fat diet in Test Example 2.

The circadian rhythm regulatory agent of Example 4 (i.e., the alkylresorcinol-containing ethanolic bran extract) was evaluated for the influence on drinking activity rhythm in mice fed a high-fat diet in accordance with the following test method. The drinking activity data were collected for every 6 hours (L1: first part of a light period; L2: second part of a light period; DE first part of a dark period; D2: second part of a dark period). The results are shown in FIG. 4, in which ND refers to a group of mice fed a normal diet; HF refers to a group of mice fed a high-fat diet; and HFAR refers to a group of mice fed a high-fat diet containing 0.5 mass % alkylresorcinol-containing ethanolic bran extract.

As is apparent from FIG. 4, the group fed a normal diet had a larger amount of activity in the first part of the dark period than in the second part of a dark period (morningness) and that the group fed a high-fat diet had a larger amount of activity in the second part of the dark period than in the first part of the dark period (eveningness). The diet containing 0.5 mass % alkylresorcinol-containing ethanolic bran extract proves to change the chronotype of the mice fed a high-fat diet in drinking behavior from eveningness to morningness.

The mice were then housed under constant dark conditions to record the drinking behavior rhythm cycles. As is apparent from Table 1, the cycle is shortened in the group given the circadian rhythm regulatory agent (alkylresorcinol-containing ethanolic bran extract) with significance compared with the group fed a normal diet and the group fed a high-fat diet. The suppression of the increase in amount of activity in the second part of the dark period is related to the shortening of the circadian rhythm cycle. Thus, the tendency to eveningness caused by a high-fat diet loading can be reformed through a series of the tests.

Seeing that the cycle is significantly shortened by the uptake of the circadian rhythm regulatory agent compared with the intake of ND or HF, the uptake of the circadian rhythm regulatory agent proves effective in promoting waking early and alleviating delayed sleep-phase syndrome caused by a long circadian clock cycle.

Test Method:

The normal diet (ND) was D12450B (rodent diet with 10% (kcal %) fat, from Research Diets, Inc.). The high-fat diet (HF) was D12492 (rodent diet with 60% (kcal %) fat, from Research Diets, Inc.). The alkylresorcinol-containing ethanolic bran extract was added to the high-fat diet in an amount of 0.5 mass %.

The mice were individually housed throughout the testing. The drinking activity data of the mice were collected using Chronobiology Kit software from Stanford Software Systems, CA.

Four-week-old male C57BL/6J Jms Sic mice (from Japan SLC, Inc.) were acclimated to light/dark cycles (12-hour light period and 12-hour dark period; lighting from 0:00 to 12:00) for two weeks. After the acclimation, the mice were divided into three groups: a group fed a normal diet (n=6), a group fed a high-fat diet (n=6), and a group fed a high-fat diet containing the alkylresorcinol-containing ethanolic bran extract (n=5), and fed ad lib. for 10 weeks. After the 10-week feeding, the mice were kept under constant dark conditions, and the drinking activity data were collected.

TABLE 1

|  | ND | HF | HFAR |
|---|---|---|---|
| Period (hr) | 23.94 ± 0.03 | 23.91 ± 0.03 | 23.83 ± 0.00* |

*$P < 0.05$ vs. ND and HF diet

Test Example 3

The circadian rhythm regulatory agent of Example 4 (alkylresorcinol-containing ethanolic bran extract) was evaluated for the influence on corticosterone secretion in mice fed a high-fat diet according to the following test method. The results are shown in FIG. 5.

Figure 5:
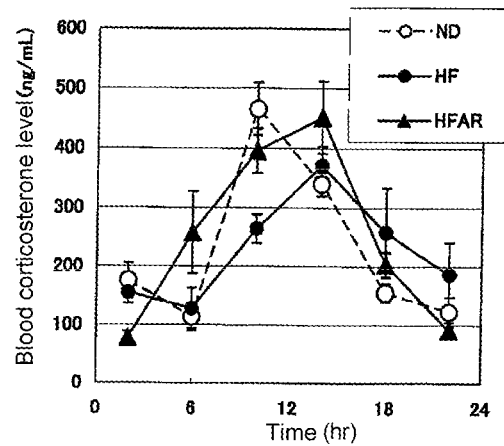
FIG. 5 is a graph showing the influence of the alkylresorcinol-containing ethanolic extract of the bran on corticosterone secretion in mice fed a high-fat diet in Test Example 3.

As is apparent from FIG. 5, the corticosterone level in blood varies diurnally in the normal diet-fed group, showing the highest peak immediately before the dark period. It is seen that the high-fat diet-fed group shows a delay of the peak (phase delay) and a decrease of the amplitude of the diurnal variation. The diet containing 0.5 mass % alkylresorcinol-containing ethanolic bran extract proves to be effective in counteracting the phase delay and the decrease of the amplitude in blood corticosterone rhythm.

Test Method:

The normal diet (ND) was D12450B (rodent diet with 10% (kcal %) fat, from Research Diets, Inc.). The high-fat diet (HF) was D12492 (rodent diet with 60% (kcal %) fat, from Research Diets, Inc.). The alkylresorcinol-containing ethanolic bran extract was added to the high-fat diet in an amount of 0.5 mass %.

Four-week-old male C57BL/6J Jms Sic mice (from Japan SLC, Inc.) were acclimated to light/dark cycles (12-hour light period and 12-hour dark period; lighting from 0:00 to 12:00) for two weeks. After the acclimation, the mice were divided into three groups each consisting of 24 mice: a group fed a normal diet, a group fed a high-fat diet, and a group fed a high-fat diet containing the alkylresorcinol-containing ethanolic bran extract, and fed ad lib. for 10 weeks.

Four mice per group were sacrificed every 4 hours from 10:00, their whole blood samples were collected, and the blood plasma was separated. The plasma samples were stored at −80° C. in their frozen state. The blood corticosterone level was determined using a commercially available kit (Assay Pro, St. Charts, MOo.).

Test Example 4

The circadian rhythm regulatory agent of Example 4 (alkylresorcinol-containing ethanolic bran extract) was evaluated for the influence on wheel running activity in stressed mice according to the test method below. The results are shown in FIG. 6.

Figure 6:
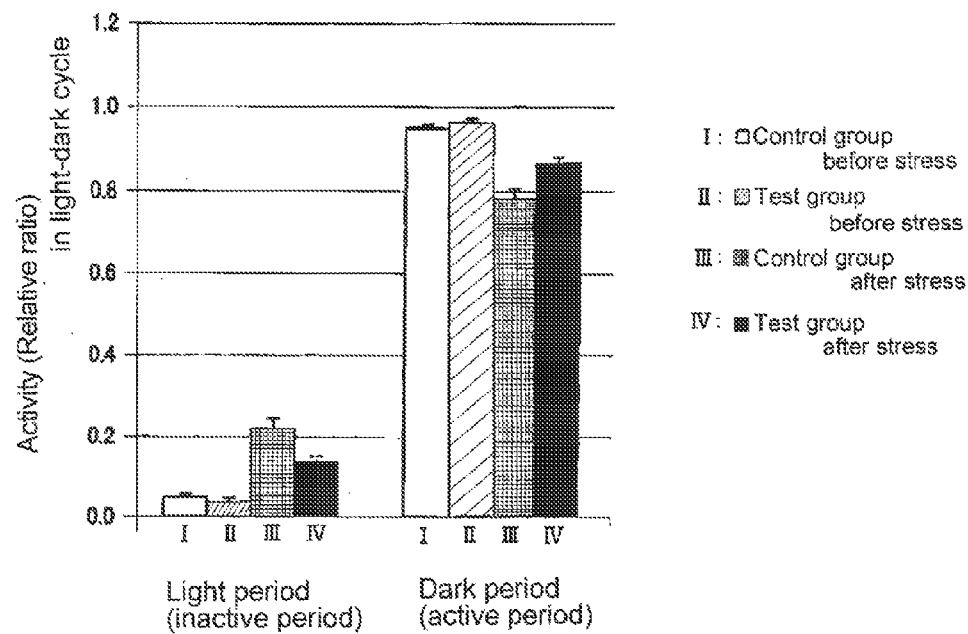
FIG. 6 is a graph showing the influence of the alkylresorcinol-containing ethanolic extract of the bran on wheel-running activity in stressed mice in Test Example 4.

As is apparent from FIG. 6, the diet containing 0.5 mass % alkylresorcinol-containing ethanolic bran extract proves to be effective in suppressing the increase in amount of activity in the light period in the mice having stress-related sleep disorder.

Test Method:

A powdered diet AIN-93M (from Oriental Yeast Co., Ltd.) was blended with 0.5 mass % alkylresorcinol-containing ethanolic bran extract, and the blend diet was pelletized to prepare a test diet. Pelletized AIN-93M was used as a control.

The mice were individually housed in a cage equipped with a running wheel (SW-15s, from Melquest, Ltd.) throughout the testing. The activity data of the mice were collected using Chronobiology Kit software (Stanford Software Systems, CA).

Four-week-old male S1c:B6C3F1 mice (from Japan SLC, Inc.) were bred in light/dark cycles (12-hour light period and 12-hour dark period; lighting from 0:00 to 12:00). Mice were fed ad lib. for 4 weeks (non-stress period) with AIN-93M containing the alkylresorcinol-containing ethanolic bran extract in the test group (alkylresorcinol group) consisting of 12 mice and with AIN-93M in the control group consisting of 11 mice.

After the non-stressed feeding experience, the mice were physically inhibited from getting out of the wheel thereby to continuously induce a stress-related sleep disorder for 2 weeks (stress period). The mice having the stress-related sleep disorder show a rhythm disorder that can be extrapolated to general sleep disorders. For example, an increase in activity in the daytime (light period), which is naturally the inactive period for mice as the nocturnal animal, and a decrease in activity in the night (dark period), which is the active period for mice, are observed.

Test Example 5

Figure 7:
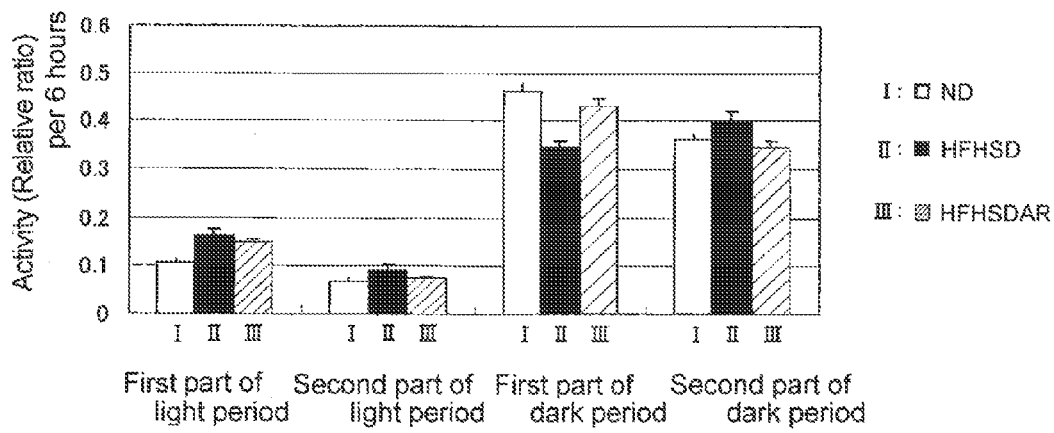
FIG. 7 is a graph showing the influence of the alkylresorcinol-containing ethanolic extract of the bran on drinking behavior rhythm in mice fed a high-fat high-sucrose diet in Test Example 5.

The circadian rhythm regulatory agent of Example 4 (i.e., the alkylresorcinol-containing ethanolic bran extract) was evaluated for the influence on drinking behavior rhythm in mice fed a high-fat high-sucrose diet in accordance with the following test method. The diurnal drinking activity data were collected for every 6 hours (L1: first part of a light period; L2: second part of a light period; D1: first part of a dark period; D2: second part of a dark period). The results are shown in FIG. 7, in which ND refers to a group of mice fed a normal diet; HFHSD refers to a group of mice fed a high-fat high-sucrose diet; and HFHSDAR refers to a group of mice fed a high-fat high-sucrose diet containing 0.5 mass % alkylresorcinol-containing ethanolic bran extract.

As is apparent from FIG. 7, although the group fed a high-fat high-sucrose diet had an increased amount of activity in the light period compared with the group fed a normal diet, the increase in activity in the light period in the high-fat high-sucrose diet-fed mice is suppressed by the blend diet with 0.5 mass % alkylresorcinol-containing ethanolic bran extract. Furthermore, the phenomenon of increasing activity in D2 compared with D1 in the high-fat high-sucrose diet-fed mice (the tendency to eveningness) is reformed by the alkylresorcinol-containing ethanolic bran extract with significance.

Test Method:

AIN-93M (containing milk casein, available from Oriental Yeast Co., Ltd.) was used as the normal diet. F2HFHSD (from Oriental Yeast) was used as the high-fat high-sucrose diet (HFHSD). The high-fat high-sucrose diet was blended with 0.5 mass % alkylresorcinol-containing ethanolic bran extract.

The drinking activity data of the mice were collected throughout the testing using Chronobiology Kit software (Stanford Software Systems, CA).

Four-week-old male C57BL/6J Jms Sic mice (from Japan SLC, Inc.) were acclimated to light/dark cycles (12-hour light period and 12-hour dark period; lighting from 0:00 to 12:00) for two weeks. After the acclimation, the mice were divided into three groups: a group fed a normal diet (9 cages), a group fed a high-fat high-sucrose diet (9 cages), and a group fed a high-fat high-sucrose diet containing the alkylresorcinol-containing ethanolic bran extract (9 cages) and fed ad lib. for 6 weeks.

The invention claimed is:

1. A method of regulating the circadian rhythm of a human, comprising steps of:

providing a pharmaceutical composition, comprising as an active ingredient a plant extract comprising an alkylresorcinol of general formula (1):

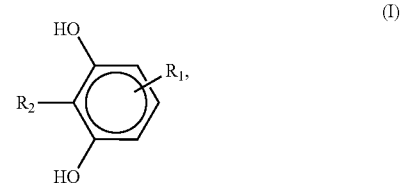

wherein $R_1$ is a saturated or unsaturated C15-C27 alkyl group; and $R_2$ is a hydrogen atom or a methyl group; and administering to said human an effective amount in a range of 0.01 to 10 g per day of the pharmaceutical composition.

2. The method according to claim 1, wherein the plant extract comprises a combination of:
1,3-Dihydroxy-5-n-pentadecylbenzene,
1,3-Dihydroxy-5-n-heptadecylbenzene,
1,3-Dihydroxy-5-n-nonadecylbenzene,
1,3-Dihydroxy-5-n-heneicosylbenzene,
1,3-Dihydroxy-5-n-tricosylbenzene, and
1,3-Dihydroxy-5-n-pentacosylbenzene.

* * * * *